US011293008B2

(12) United States Patent
LaBarge et al.

(10) Patent No.: US 11,293,008 B2
(45) Date of Patent: Apr. 5, 2022

(54) MEDIA FOR CULTURING EPITHELIAL CELLS

(71) Applicant: The Regents of the University of California, Oakland, CA (US)

(72) Inventors: Mark A. LaBarge, Orinda, CA (US); Martha R. Stampfer, Oakland, CA (US); James C. Garbe, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 354 days.

(21) Appl. No.: 15/762,517

(22) PCT Filed: Sep. 23, 2016

(86) PCT No.: PCT/US2016/053510
§ 371 (c)(1),
(2) Date: Mar. 22, 2018

(87) PCT Pub. No.: WO2017/053845
PCT Pub. Date: Mar. 30, 2017

(65) Prior Publication Data
US 2019/0352606 A1 Nov. 21, 2019

Related U.S. Application Data

(60) Provisional application No. 62/232,294, filed on Sep. 24, 2015.

(51) Int. Cl.
*C12N 5/071* (2010.01)
(52) U.S. Cl.
CPC ........ *C12N 5/0631* (2013.01); *C12N 2500/14* (2013.01); *C12N 2500/32* (2013.01); *C12N 2500/34* (2013.01); *C12N 2500/35* (2013.01); *C12N 2500/38* (2013.01); *C12N 2500/46* (2013.01); *C12N 2500/60* (2013.01)

(58) Field of Classification Search
CPC .............. C12N 5/0631; C12N 2500/14; C12N 2500/32; C12N 2500/34; C12N 2500/35; C12N 2500/38; C12N 2500/46; C12N 2500/60
See application file for complete search history.

(56) References Cited

U.S. PATENT DOCUMENTS

| 4,423,145 | A | 12/1983 | Stampfer et al. |
| 4,808,532 | A | 2/1989 | Stampfer |
| 8,936,939 | B2 | 1/2015 | Ince et al. |
| 8,962,325 | B2 | 2/2015 | Stampfer et al. |
| 2013/0055417 | A1 | 2/2013 | Ince et al. |
| 2013/0323837 | A1* | 12/2013 | Judd .................. C12N 5/0629 435/375 |
| 2015/0247121 | A1 | 9/2015 | Stampfer et al. |

OTHER PUBLICATIONS

Hammond et al., "Serum-free growth of human mammary epithelial cells: Rapid clonal growth in defined medium and extended serial passage with pituitary extract", 1984, Proceedings of the National Academy of Sciences of the United States of America 81, p. 5435-5439.*
Stampfer et al., "Chapter 4: Culture of Human Mammary Epithelial Cells", 2002, Culture of Epithelial Cells, 2nd Ed, p. 94-135.*
Peehl, "Chapter 6: Human Prostatic Epithelial Cells", 2002, Culture of Epithelial Cells, 2nd Ed., p. 171-194.*
Evans et al., "Studies of Nutrient Media for Tissue Cells in Vitro: I. A Protein-free Chemically Defined Medium for Cultivation of Strain L Cells", 1956, The Journal of Cancer Research 16(1), p. 77-86.*
Matthews et al., "Chemically Defined Medium for the Growth of Lymphocytes", 1987, Methods in Enzymology 150, p. 134-146.*
Shipley et al., "Improved Medium and Culture Conditions for Clonal Growth With Minimal Serum Protein and for Enhanced Serum-Free Survival of Swiss 3T3 Cells", 1981, In Vitro vol. 17(8), p. 656-670.*
Afanasieva et al. (2012) "Psychostimulant and nootropic effect of major and trace element composition" Bull Exp Biol Med; 154(2):224-227.
Ashokkumar et al. (2007) "Effect of folate oversupplementation on folate uptake by human intestinal and renal epithelial cells" Am J Clin Nutr; 86(1):159-166.
Garbe et al. (2009) "Molecular distinctions between the stasis and telomere attrition senescence barriers demonstrated by long-term culture of normal human mammary epithelial cells" Cancer Res; 69(19)7557-7568.
Garbe et al. (2012) "Accumulation of Multipotent Progenitors with a Basal Differentiation Bias during Aging of Human Mammary Epithelia," Cancer Research 72(14):3687-3701.
Hammond et al. (1984) "Serum-free growth of human mammary epithelial cells: rapid clonal growth in defined medium and extended serial passage with pituitary extract" Proc Natl Acad Sci USA; 81(17):5435-5439.
Jerums and Yang (2005) "Optimization of Cell Culture Media," Bioprocess International Supplement, 38-44.
Labarge et al. (2013) "Processing of Human Reduction Mammoplasty and Mastectomy Tissues for Cell Culture" J Vis Exp; 71:e50011.
Stampfer (1982) "Cholera toxin stimulation of human mammary epithelial cells in culture" In Vitro; 18(6):531-537.

* cited by examiner

*Primary Examiner* — Christopher M Babic
*Assistant Examiner* — Alexander W Nicol
(74) *Attorney, Agent, or Firm* — Shweta Chandra; Bozicevic, Field & Francis LLP

(57) ABSTRACT

A method of growing primary human epithelial cells, in particular human epithelial cells using a basal formula containing individual (a) amino acids, (b) vitamins, (c) trace elements, and (d) other organics such as linoleic acid. The basal medium may be a mixture of amino acids, vitamins, and salts that constitute the basic media that is used to culture epithelial cells over a number of population doublings, e.g., over at least one week, while maintaining a normal phenotype and exerting low stress on the cultured cells, and maintaining lineage heterogeneity.

9 Claims, 7 Drawing Sheets

|  | M87A | 1:1 mixture of commercial media |
| --- | --- | --- |
| Best-fit values |  |  |
| Slope | 0.9670 ± 0.006351 | 1.044 ± 0.1025 |
| Y-intercept when X=0.0 | -0.01833 ± 0.04099 | 0.7783 ± 0.7282 |
| X-intercept when Y=0.0 | 0.01896 | -0.7455 |

MEDIA FOR CULTURING EPITHELIAL CELLS

CROSS-REFERENCE TO RELATED APPLICATIONS

This application claims the benefit of U.S. Provisional Patent Application Ser. No. 62/232,294, filed Sep. 24, 2015, the disclosure of which is herein incorporated by reference in its entirety.

STATEMENT OF GOVERNMENTAL SUPPORT

This invention was made with Government support under contract AG040081 awarded by the National Institutes of Health, and under Contract Number DE-ACO2-05CH11231 between the U.S. Department of Energy and The Regents of the University of California for the management and operation of the Lawrence Berkeley National Laboratory. The Government has certain rights in the invention.

BACKGROUND OF THE INVENTION

Field of the Invention

The present invention relates to the field of cell culture, in particular to culture media for epithelial cell cultures, e.g., human mammary epithelial cell cultures.

Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

Access to and ability to culture normal human mammary epithelial cells (HMEC) is essential for experiments that seek to understand the many differences between normal and abnormal mammary epithelia. The methods used to establish HMEC in culture impact the definition of normal. Thus, a comparison of HMEC strains established in parallel using different culture media can facilitate an understanding of the normal state and the changes that lead to an abnormal state.

Cell culture is a method for growing or maintaining cells in vitro under controlled conditions. Primary cell cultures refer to dispersed cells that are cultured directly from tissues and have limited lifespan, whereas cell lines refer to immortalized cells that can be cultured indefinitely. Normal human epithelial cells in culture have generally shown a limited proliferative potential of ~10-40 population doublings before encountering a stress-associated senescence barrier (stasis) associated with elevated levels of cyclin-dependent kinase inhibitors p16 and/or p21.

Chemically defined basal liquid cell culture media are used to provide nutrients for cell growth in research, diagnostic and manufacturing applications. Typical cell culture media contain a mixture of defined nutrients dissolved in a buffered physiological saline solution. Most culture media contain salts, amino acids, sugar, vitamins and other organic nutrients. The basal media is used as a starting point for the addition of various supplements to generate a complete growth medium.

The selection of a basal cell medium for cell culture applications is primarily dependent on the chemical definition of the basal medium, the type of cell to be grown, and the culture system being employed.

Specific Patents and Publications

Stampfer et al, "Enhanced growth medium and method for culturing human mammary epithelial cells," U.S. Pat. No. 4,423,145, discloses methods for isolating and culturing human mammary epithelial cells of both normal and malignant origin.

Stampfer et al., "Increasing cell culture population doublings for long-term growth of finite life span human cell cultures," U.S. Pat. No. 8,962,325 discloses a cell culture medium for culturing pre-stasis human mammary epithelial cells (HMEC), the medium being a mixture of two media, (i) and (ii), namely a medium (i) with serum, that is one of MM or MM4 medium and (ii) a different, serum-free medium, with defined ingredients for growth of human mammary epithelial cells, the mixture containing 30% to 60% of medium (i) and 40% to 70% of serum free medium (ii), the culture medium further comprising between about 0.05 nM and about 5.0 nM of an anti-stress associated compound that is oxytocin.

Stampfer et al., "Continuous human cell lines and method of making same," U.S. Pat. No. 4,808,532, discloses substantially genetically stable continuous human cell lines derived from normal human mammary epithelial cells (HMEC). In MM medium, mitotic activity in pre-stasis HMEC was visible after forty-eight hours, and there was subsequent rapid growth to near confluence within 5-8 days after seeding. The deposited cell lines of the present invention were derived from cells grown in the MM medium. Pre-stasis cell growth in MCDB170 medium was slower, 10-14 days being required to achieve confluence (cells grown in this latter medium were not used to provide the deposited cells lines of the subject invention, although equivalent cells lines may emerge using MCDB170).

Hammond et al., Proc. Natl. Acad. Sci. USA Vol. 81, pp. 5435-5439, September 1984, "Serum-free growth of human mammary epithelial cells: Rapid clonal growth in defined medium and extended serial passage with pituitary extract," discloses an optimized basal nutrient medium, MCDB170. As disclosed there, MCDB170 is supplemented with insulin, hydrocortisone, epidermal growth factor, ethanolamine, phosphoethanolamine, and bovine pituitary extract. Replacement of pituitary extract with prostaglandin E1 and ovine prolactin yields a defined medium that supports rapid clonal growth and serial subculture for three or four passages.

Ince et al., "Hormone responsive tissue culture system and uses thereof," U.S. Pat. No. 8,936,939 discloses a medium that supports growth and/or proliferation of primary breast epithelial progenitor cells without detectable genetic alterations.

A medium "171" is commercially available from ThermoFisher Scientific, described at https(colon slash slash) www(dot) thermofisher(dot) com/order/catalog/product/M171500.

A medium MEBM/MEGM is available from Lonza http (colon-slash-slash) www(dot) lonza.com/products-services/bio-research/primary-cells/human-cells-and-media/mammary-epithelial-cells-and-media/megm-mammary-epithelial-cell-growth-medium.aspx

BRIEF SUMMARY OF THE INVENTION

The following brief summary is not intended to include all features and aspects of the present invention, nor does it imply that the invention must include all features and aspects discussed in this summary.

In certain aspects, the present invention comprises a method and mixture comprising individual components. Accordingly, the present invention provides a useful collection of defined stock solutions useful for making a basal medium for low stress culture of normal human epithelial cells, comprising: (a) a solution of 20 naturally occurring amino acids; (b) a solution of vitamins including folic acid; (c) a solution of trace elements including calcium chloride; (d) a solution of other organics, including adenine, choline chloride, D-glucose myo-inositol, putrescine 2HCl, sodium pyruvate, and thymidine; and (e) a solution of HEPES (4-(2-hydroxyethyl)-1-piperazineethanesulfonic acid) buffer, NaOH, D-glucose and phenol red (optional), wherein the defined stock solutions (a) through (e) are suitable for combination into the basal medium. The inventive components are further elaborated in Table 1.

In certain aspects, the present invention comprises a basal medium comprising: (a) 20 naturally occurring amino acids, including L-arginine hydrochloride in an amount between 90 and 120 mg/L; (b) vitamins including folic acid in an amount of between 1 and 1.5 mg/L; (c) trace elements including calcium chloride in an amount between 190 and 220 mg/L; (d) other organics, including adenine, choline chloride, D-glucose (1700-2500 mg/L), myo-inositol, putrescine 2HCl, sodium pyruvate, and thymidine; and (e) HEPES buffer, NaOH, D-glucose (1000-2000 mg/L) and phenol red (optional), provided that values given in mg/L are mg in distilled water and may be varied by plus or minus an insignificant amount, e.g. 5%, 10%, 15% or 20%, on a component by component basis.

In certain aspects, the present invention comprises the components as defined in Table 1, provided that phenol red is optional.

In certain aspects, the present invention comprises an optimized or complete media prepared from the basal medium and comprising serum and growth factor supplements. In certain aspects, the present invention comprises the ingredients of Table 3 and Table 3A.

In certain aspects, the present invention comprises a medium as described above free of conditioned medium.

In certain aspects, the present invention comprises a method for preparing the present defined basal medium, comprising the step of preparing solutions of elements (a) through (e) separately and combining individually as separate stock solutions.

In certain aspects, the present invention comprises culturing normal human epithelial cells, comprising the step of culturing the normal human epithelial cells with a culture medium comprising a basal medium as described above, for a period of time that causes at least 10 population doublings of the normal human epithelial cells.

Aspects of the present disclosure include a combination of defined stock solutions for making a basal medium, useful for low stress culture of normal human epithelial cells, including (a) a solution of 20 naturally occurring amino acids; (b) a solution of vitamins including folic acid; (c) a solution of trace elements including calcium chloride; (d) a solution comprising adenine, choline chloride, D-glucose myo-inositol, putrescine 2HCl, sodium pyruvate, and thymidine; and (e) a solution of HEPES buffer, NaOH, and D-glucose, where the defined stock solutions (a) through (e) are suitable for combination into the basal medium. In certain aspects, the solution of HEPES buffer, NaOH, and D-glucose further comprises phenol red. Also provided is a basal medium comprising a mixture of stock solutions (a) through (e) as set forth above. In certain aspects, the basal medium consists essentially of a mixture of stock solutions (a) through (e) as set forth above. Also provided is an optimized cell culture medium including a basal medium as set forth above, and serum, a growth factor, or both. Such an optimized cell culture medium may include serum and a growth factor.

Aspects of the present disclosure include methods of making a basal medium useful, e.g., for low stress culture of epithelial cells, including combining: (a) a solution of 20 naturally occurring amino acids; (b) a solution of vitamins including folic acid; (c) a solution of trace elements including calcium chloride; (d) a solution comprising adenine, choline chloride, D-glucose myo-inositol, putrescine 2HCl, sodium pyruvate, and thymidine; and (e) a solution of HEPES buffer, NaOH, and D-glucose, in a container to produce a mixture of a basal medium useful for low stress culture of epithelial cells. Such methods may further include, prior to the combining, preparing solutions (a) to (e) separately. In certain aspects, the solution of HEPES buffer, NaOH, and D-glucose further includes phenol red. According to certain embodiments, the methods further include, after the combining, sterilizing the basal medium. In certain aspects, the methods further include, after the combining, culturing epithelial cells in a medium comprising the basal medium. According to certain embodiments, the epithelial cells are cultured for from 1 to 60 population doublings, such as from 1 to 10, 10 to 20, 20 to 30, 30 to 40, 40 to 50, or 50 to 60 population doublings (e.g., for from 5 to 60, 10 to 60, 15 to 60, 20 to 60, 25 to 60, 30 to 60, 35 to 60, 40 to 60, 45 to 60, 50 to 60, or 55 to 60 population doublings). In certain aspects, during the culturing, a normal phenotype of the cells is maintained, the cultured cell are under low stress, and/or lineage heterogeneity is maintained. According to certain embodiments, the epithelial cells are normal epithelial cells. In certain aspects, the epithelial cells are human mammary epithelial cells (HMEC).

DETAILED DESCRIPTION

Definitions

Figure 1:
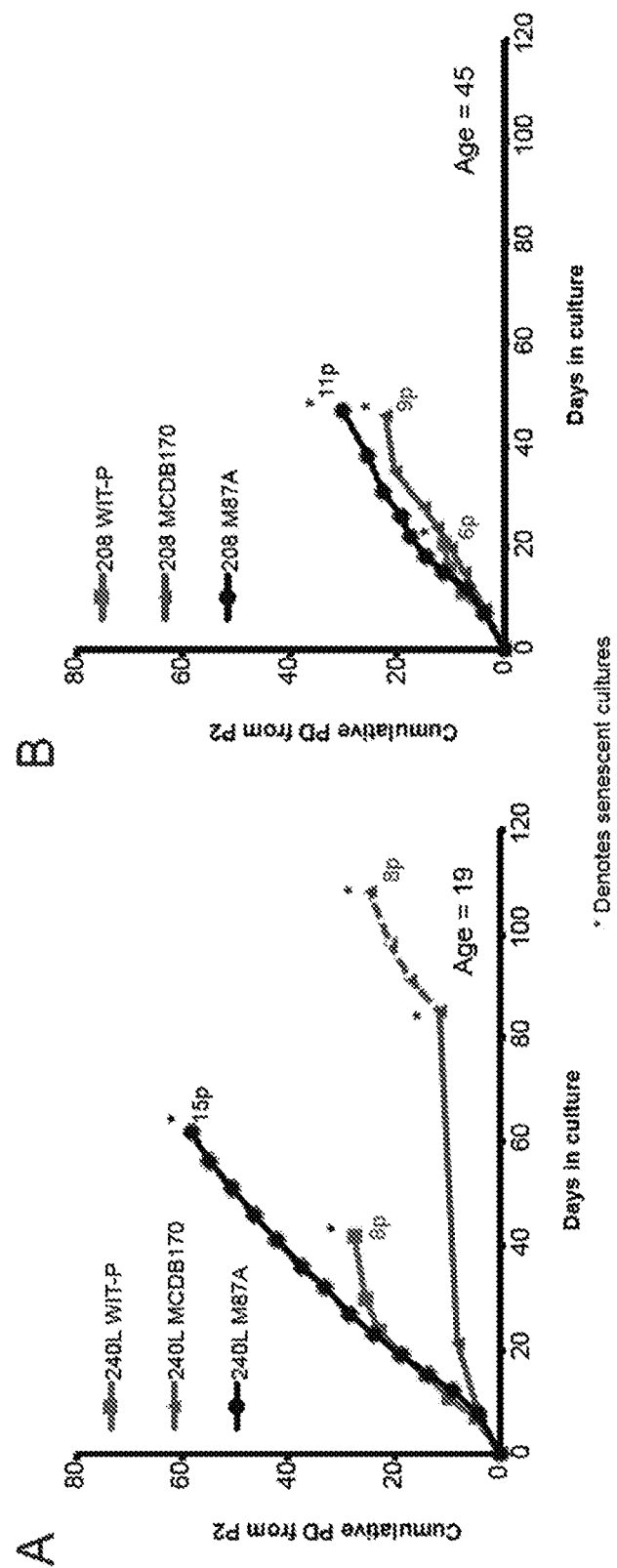
FIG. 1 shows a comparison of HMEC growth curves in pre-stasis strains established from two different breast tissue samples in three different media in parallel. Curves showing population doublings as a function of time in days for HMEC strains established from specimens 240 L (panel A) and (B) 208 (panel B), who were age 19 and 45 years at the time of reduction mammoplasty, respectively. Squares are cultures grown in WIT-P, triangles denote growth in MCDB170, and circles denote growth in M87A. In (A) MCDB170 caused characteristically rapid induction of stasis by $5^{th}$ passage, follow by emergence of a clonal post-selection post-stasis finite culture denoted by the dashed line. Asterisks denote when cultures were senescent. Panels C and D show p16 protein expression at passage 4 in pre-stasis cultures grown in M87A, MCDB170, or WIT-P media. Immunohistochemical staining of p16 (brown precipitate) in strains derived from specimen 208 (panel C) and (B) 240 L (panel D).
Figure 1:
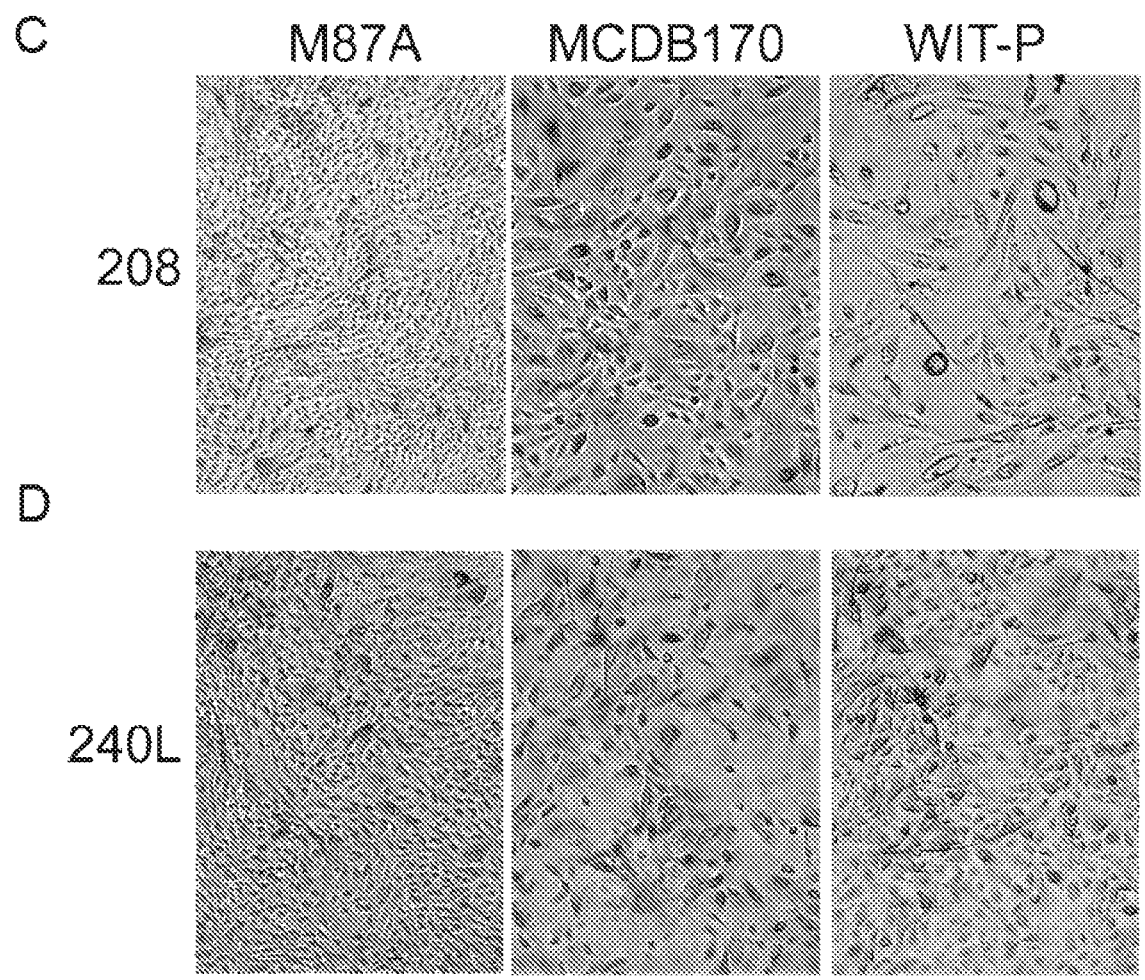

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

Ranges: For conciseness, any range set forth is intended to include any sub-range within the stated range, unless otherwise stated. A subrange is to be included within a range even though no sub-range is explicitly stated in connection with the range. As a non-limiting example, a range of 120 to 250 includes a range of 120-121, 120-130, 200-225, 121-250 etc.

The term "about" has its ordinary meaning of approximately and may be determined in context by experimental variability. In case of doubt, "about" means plus or minus 5% of a stated numerical value.

The term "basal medium" means cell culture medium that contains no supplements such as growth factors and cytokines.

The term "optimized culture medium" refers to a serum-free medium engineered specifically for the culture of Human Mammary Epithelial Cells (HMEC). This contains a basal medium plus supplements such as growth factors and other components. These could include components such as epidermal growth factor, hydrocortisone, isoproterenol, transferrin, and insulin, and bovine pituitary extract. A further explanation of an optimized culture medium is found in Jerums and Yang, "Optimization of Cell Culture Media," Bioprocess International Supplement, June 2005, pp. 38-44.

The term "HMEC" refers to human mammary epithelial cells, and generally refers to primary cells obtained from humans and includes mammary epithelial cells in any stage of the cell hierarchy. See Garbe et al., "Accumulation of Multipotent Progenitors with a Basal Differentiation Bias during Aging of Human Mammary Epithelia," Cancer Research 72(14):3687-3701 (2012).

The term "naturally occurring amino acids" refers to the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine).

The term "vitamin" is used in the common sense and may include thiamine (vitamin B1) and vitamin B12. In certain embodiments it may include folic acid.

Overview

Provided here are low cost basic growth media capable of long-term culturing of human epithelial cells. The cell culture media disclosed herein have been developed to support the exploration of normal human cells and tissues and the transformation of normal cells to malignant states. The cell culture media may support up to 60 population doublings of normal human mammary epithelial cells.

One formulation, referred to herein as M87A basal media ("A" indicating AlbuMAX® albumin) or M87A-BM, is, in one embodiment, a mixture of 63 amino acids, vitamins, and salts that constitute the basic media that may be supplemented (e.g., with growth factors) and used to culture normal human epithelial cells. These designations are used for convenience and may not be the same as other media having similar designations.

It is possible, but not desirable, to prepare a somewhat similar basal M87A-BM by using simply a 1:1 mixture of commercially available media such as DMEM/F12 and MEBM or M171 (or other MCDB170-type media). However, the compositions of many commercial media are proprietary in some cases. For details on MEBM, see, for example, Lonza Products & Services at http (colon slash slash) www (dot) lonza.com/products-services/bio-research/primary-cells/human-cells-and-media/mammary-epithelial-cells-and-media/megm-mammary-epithelial-cell-growth-medium.aspx. For details on M171, see, for example, https (colon slash slash) www (dot) thermofisher.com/order/catalog/product/M171500.

An example composition of DMEM/F12 is given in Table 4 in the comparative example below. Details on DMEM/F12 may also be found, for example, at Lonza Products & Services at http (colon slash slash) www (dot) lonza.com/products-services/bio-research/cell-culture-products/classical-media/dmem/dmem-F12-11-mixture.aspx.

The MCDB170 medium is commercially available and has been characterized in Hammond, S L, Ham, R G, and Stampfer, M R, Serum-free growth of human mammary epithelial cells: rapid clonal growth in defined medium and extended serial passage with pituitary extract, *Proc Natl Acad Sci* (USA) 81:5435-5439, 1984. Methods describing the use of this medium in the isolation and growth of human cell cultures are also described in Stampfer, M R, Isolation and growth of human mammary epithelial cells. *J Tissue Cult. Meth.* 9:107-116, 1985, hereby incorporated by reference.

An important distinction between the present defined media, using commercially readily available single molecule components, and combined commercial media is that the present methods and material ensures regularity and consistency in cell culture results.

In addition, the defined medium, using single components, offers equivalent or superior growth of human mammary epithelial cells at a significantly lower cost.

The present invention concerns the growth in culture of normal human mammary epithelial cells, e.g. non-cancerous, finite lifespan, pre-stasis cell strains, including human mammary epithelial cells (HMEC) 184D and others, obtained from reduction mammoplasty (see, Garbe J C, Bhattacharya S, Merchant B, Bassett E, Swisshelm K et al. (2009) "Molecular distinctions between stasis and telomere attrition senescence barriers shown by long-term culture of normal human mammary epithelial cells," Cancer Res 69: 7557-7568), and immortal derivatives of normal HMEC such as 184A1 and MCF10A cells and other cell lines, etc.

The present invention further provides a basal medium comprising a defined mixture of (a) amino acids including both L-cysteine HCl and L-cysteine HCl—H2O and Valine (44 mg/L); (b) vitamins, including folic acid (1.3 mg/L) biotin and D-calcium pantothenate; (c) trace elements such as $H_2SeO_3$ and (d) other organics such as linoleic acid.

The present basal medium contains amino acids, vitamins, trace elements and other ingredients that may be found in media such as DMEM/F12 or MCDB-170. However, the concentrations of the present basal medium (termed in the tables "M87A" basal media or "M87A-BM") differ from either existing medium in the concentrations of the 63 amino acids, vitamins, and salts that constitute known individual basal media. The present basal media may be further combined with media supplements such as fetal bovine serum, bovine pituitary extract, insulin, isoproterenol, hydrocortisone, apo-transferrin, oxytocin, cholera toxin, epidermal growth factor, β-estradiol, tri-iodo-thyronine, and albumin. This is termed a complete medium (See Table 3A).

In certain aspects, the present basal medium is made from individual compounds, e.g. separately mixing the individual glycine, L-alanine, arginine hydrochloride, L-asparagine-H2O etc. in a number of individual stock solutions and then combining the stock solutions. Individual stock solutions of (a) phenol red, (b) NaOH, (c) amino acids-1, (d) vitamins, (e) L-glutamine, (f) sodium pyruvate (g) L-cysteine, (h) amino acids-2, (i) adenine, myo-inositol, lipoic acid, thymidine, and putrescine; (j) $CaCl_2$ $2H_2O$; (k1) $MgSO_4$ $7H_2O$; (k2) $FeSO_4$ $7H_2O$; (l) $CuSO_4$ $5H_2O$, $H_2SeO_3$, $MnSO_4$ $5H_2O$, $NaSiO_3$ $9$ $H_2O$, $(NH_4)_6Mo_7O_{24}$-$4H_2O$, $NH_4VO_3$, $NiCl_2$ $6H_2O$, $SnCl_2$ $2H_2O$, and $ZnSO_4$·$7H_2O$ (m) riboflavin; and (n) individually adding remaining ingredients.

The present cell culture medium supports the growth of multiple lineages of normal human mammary epithelial cells (HMEC), such as luminal epithelial and myoepithelial cells, over a number of population doublings. This has been demonstrated by a calculation of Shannon diversity indices that compared cultures of normal pre-stasis HMEC grown in M87A versus two commercial defined media MCDB170 and WIT-P that showed greater cellular heterogeneity was maintained over multiple passages in M87A.

EXAMPLES

Example 1—Composition of Basal Medium from Individual Components

In one embodiment of the present invention, the basal medium has a composition as shown in the following table:

TABLE 1

| Component | Concentration (in mg/L of distilled de-ionized water) |
| --- | --- |
| Glycine | 13.1285 |
| L-Alanine | 6.6795 |
| L-Arginine hydrochloride | 105.355 |
| L-Asparagine-$H_2O$ | 78.8 |
| L-Aspartic acid | 9.98 |
| L-Cysteine hydrochloride-$H_2O$ | 14.925 |
| L-Cystine 2HCl | 15.645 |
| L-Glutamic Acid | 11.03 |
| L-Glutamine | 328.6 |
| L-Histidine hydrochloride-$H_2O$ | 26.225 |
| L-Isoleucine | 33.795 |
| L-Leucine | 49.205 |
| L-Lysine hydrochloride | 63.895 |
| L-Methionine | 10.858 |
| L-Phenylalanine | 20.218 |
| L-Proline | 11.5025 |
| L-Serine | 28.89 |
| L-Threonine | 44.59 |
| L-Tryptophan | 7.573 |
| L-Tyrosine disodium salt dihydrate | 32.425 |
| L-Valine | 44.005 |
| Biotin | 0.0054145 |
| Choline chloride | 11.47 |
| D-Calcium pantothenate | 1.23915 |
| Folic Acid | 1.328008 |
| Niacinamide | 4.0625 |
| Pyridoxine hydrochloride | 1.03084 |
| Riboflavin | 0.16595 |
| Thiamine hydrochloride | 1.25365 |
| Vitamin B12 | 0.40775 |
| Lipoic Acid | 0.0535315 |
| myo-Inositol | 15.31 |
| Calcium Chloride ($CaCl_2$) (anhyd.) | 205.3 |
| Cupric sulfate ($CuSO_4$—$5H_2O$) | 0.00077485 |
| Ferric Nitrate ($Fe(NO_3)3$"$9H_2O$) | 0.025 |
| Ferrous sulfate ($FeSO_4$—$7H_2O$) | 0.9035 |
| Magnesium Chloride (anhydrous) | 14.32 |
| Magnesium Sulfate ($MgSO_4$) (anhyd.) | 222.72 |
| Potassium Chloride (KCl) | 249.1 |
| Sodium Bicarbonate ($NaHCO_3$) | 600 |
| Sodium Chloride (NaCl) | 7004.75 |
| Sodium Phosphate dibasic ($Na_2HPO_4$) anhydrous | 35.51 |
| Sodium Phosphate monobasic ($NaH_2PO_4$—$H_2O$) | 31.25 |
| Zinc sulfate ($ZnSO_4$—$7H_2O$) | 0.2879 |
| $H_2SeO_3$ | 0.0019345 |
| $MnSO_4$ $5H_2O$ | 0.00006025 |
| Na2SiO3 $9H_2O$ | 0.07105 |
| $(NH4)_6Mo_7O_{24}$ $4H_2O$ | 0.000618 |
| $NH_4VO_3$ | 0.0002925 |
| $NiCl_2$ $6H_2O$ | 5.945E-07 |
| $SnCl_2$ $2H_2O$ | 0.000000564 |
| $KH_2PO_4$ | 34.025 |
| D-Glucose (Dextrose) | 2296.15 |
| Hypoxanthine Na | 1.26255 |
| Linoleic Acid | 0.021 |
| Putrescine 2HCl | 0.04058055 |

TABLE 1-continued

| Component | Concentration (in mg/L of distilled de-ionized water) |
|---|---|
| Sodium Pyruvate | 82.5 |
| Thymidine | 0.21883 |
| HEPES | 5361.75 |

As will be appreciated by one of skill in the art, the final concentrations of the stock solutions may be precisely as provided in Table 1, or may vary so long as the basal medium has one or more of the desirable properties described elsewhere herein, e.g., useful for low-stress culture of epithelial cells (e.g., 2-3 fold more growth of pre-stasis HMEC as compared to MCDB170 or WIT-P). For example, the final concentrations of the components in the stock solutions presented in Table 1 may independently vary (i.e., be greater than or less than) by 20% or less, 15% or less, 10% or less, 9% or less, 8% or less, 7% or less, 6% or less, 5% or less, 4% or less, 3% or less, 2% or less, or 1% or less, as compared to the final concentrations of such components as set forth in Table 1.

Example 2—Preparation of Basal Medium

In one embodiment, the present medium is prepared by adding stock solutions to water, and adding other components directly to the medium instead of from a stock solution. The stock solutions are listed in the following table as A, B, C, D, E, F, G, H, I, J, K1, K2, L, and M, with fold concentration of the stock indicated in parentheses.

TABLE 2

| Stock solution letter | Components | Molecular Weight | Concentrations in Stock g/L | Moles/L |
|---|---|---|---|---|
| A | Phenol Red | 376.36 | 0.621 | $1.65 \times 10^{-3}$ |
| B | Sodium Hydroxide | 40.01 | 80.04 | 2 |
| C (100x) | L-Arginine HCl | 210.7 | 10.5355 | $5 \times 10^{-2}$ |
| | L-Asparagine H$_2$O | 150.1 | 7.88 | $5 \times 10^{-2}$ |
| | Choline Chloride | 139.6 | 1.147 | $1 \times 10^{-2}$ |
| | L-Histidine HCl H$_2$O | 209.7 | 2.622 | $1 \times 10^{-2}$ |
| | L-Isoleucine (allo-free) | 131.2 | 3.38 | $3 \times 10^{-2}$ |
| | L-Leucine | 131.2 | 4.921 | $4 \times 10^{-2}$ |
| | L-Lysine HCl | 182.7 | 6.39 | $4 \times 10^{-2}$ |
| | L-Methionine | 149.2 | 1.086 | $7 \times 10^{-3}$ |
| | L-Phenylalanine | 165.2 | 2.027 | $1 \times 10^{-2}$ |
| | L-Proline | 115.1 | 1.15 | $1 \times 10^{-2}$ |
| | L-Serine | 105.1 | 2.89 | $3 \times 10^{-2}$ |
| | L-Threonine | 119.1 | 4.46 | $4 \times 10^{-2}$ |
| | L-Tryptophan | 204.2 | 0.757 | $4 \times 10^{-3}$ |
| | L-Tyrosine | 181.2 | 0.453 | $3 \times 10^{-3}$ |
| | L-Tyrosine Disodium Salt Dihydrate | 261 | 2.79 | $1 \times 10^{-2}$ |
| | L-Valine | 117.2 | 4.4 | $4 \times 10^{-2}$ |
| D (100X) | d-Biotin | 244.3 | 0.5 mg | $2 \times 10^{-5}$ |
| | Folinic acid (Ca 2+ Salt) | 601.6 | 0.133 | |
| | Folic Acid | 441 | 0.3 mg | |
| | Niacinamide | 122.1 | 0.407 | $3 \times 10^{-3}$ |
| | Pantothenic Acid (Hemi-calcium salt) | 238.3 | 0.124 | |
| | Pyridoxine HCl | 205.6 | 0.103 | |
| | Thiamine HCl | 227.3 | 0.126 | |
| | Vitamin B12 | 1355.4 | 0.041 | |
| E (100X) | L-Glutamine | 146.1 | 32.86 | |
| F (100X) | Sodium Pyruvate | 110 | 8.25 | |
| G (100X) | L-Cysteine HCl H2O | 175.6 | 1.492 | |
| | L-Cysteine HCl | | 1.56 | |
| H (100X) | L-Alanine | 89.09 | 0.668 | |
| | L-Aspartic acid | 133.1 | 0.998 | |
| | L-Glutamic acid | 147.1 | 1.103 | |
| | Glycine | 75.07 | 1.312 | |
| I (100X) | Adenine | 135.1 | 0.00675 | |
| | myo-inositol | 180.2 | 1.531 | |
| | Lipoic Acid | 206.3 | 0.00535 | |
| | Thymidine | 242.2 | 0.022 | |
| | Putrescine 2HCl | 161.1 | 0.004 | |
| J (200X) | CaCl$_2$ 2H$_2$0 | 147.02 | 41.06 | |
| K1 (200X) | MgSO$_4$ 7H$_2$O | 246.38 | 44.54 | |
| K2 (200X) | FeSO$_4$ 7H$_2$O | 278.02 | 0.1807 | |
| L (100X) | CuSO$_4$ 5H$_2$O | 249.68 | .077 mg | |
| | H$_2$SeO$_3$ | 128.98 | 0.19 mg | |
| | MnSO$_4$ 5H$_2$0 | 241.08 | .006 mg | |
| | NaSiO$_3$ 9 H$_2$O | 284.2 | 0.71 | |
| | (NH$_4$)MO$_7$O$_{24}$ 4H2O | 1235.89 | .062 mg | |
| | NH$_4$VO$_3$ | 116.99 | .0293 mg | |
| | NiCl$_2$ 6H$_2$O | 237.7 | 0.00006 mg | |
| | SnCl$_2$ 2H$_2$O | 225.63 | .0000564 mg | |
| | ZnSO$_4$7H$_2$O | 287.54 | 0.029 | |
| M (100X) | Riboflavin | 376.4 | 0.0166 | |

For illustration purposes, Stock A in Table 2 above may be prepared by dissolving phenol red powder in water (e.g., distilled de-ionized water) to a concentration of 0.621 grams per liter. For example, to make 250 mL of Stock A, 0.155 grams of phenol red may be dissolved in 200 mL of water, followed by bringing the resulting solution to a total volume of 250 mL with additional water.

Also for illustration purposes, Stock B may be prepared by dissolving sodium hydroxide pellets in water (e.g., distilled de-ionized water) at a concentration of 80.04 grams per liter. For example, to make 250 mL of Stock B, 20.01 grams of sodium hydroxide pellets may be dissolved in 200 mL of water, followed by bringing the resulting solution to a total volume of 250 mL with additional water.

The basal medium may include a mixture of each of the stock solutions provided in Table 2, or may include a mixture of less than all of such stock solutions so long as the basal medium has one or more of the desirable properties described elsewhere herein, e.g., useful for low-stress culture of epithelial cells (e.g., 2-3 fold more growth of pre-stasis HMEC as compared to MCDB170 or WIT-P). According to certain embodiments, the basal medium includes a mixture of 5 or more, 6 or more, 7 or more, 8 or more, 9 or more, 10 or more, 11 or more, 12 or more, 13 or more, or all 14 of the stock solutions provided in Table 2. Such a basal medium may include 1 or more, 2 or more, 3 or more, 4 or more, 5 or more, 6 or more, 7 or more, 8 or more, 9 or more, 10 or more, 11 or more, 12, or all 13 of the components provided in Table 3 directly added to the basal medium.

In related aspects, also provided by the present disclosure are methods of making a basal medium, the method including combining 5 or more, 6 or more, 7 or more, 8 or more, 9 or more, 10 or more, 11 or more, 12 or more, 13 or more, or all 14 of the stock solutions provided in Table 2, in a container to produce a mixture of a basal medium useful, e.g., for low stress culture of epithelial cells. The method may further include adding additional components directly to the resulting mixture. For example, the method may further include adding 1 or more, 2 or more, 3 or more, 4 or more, 5 or more, 6 or more, 7 or more, 8 or more, 9 or more, 10 or more, 11 or more, 12, or all 13 of the components provided in Table 3 directly to the resulting mixture.

As will be appreciated by one of skill in the art, the final concentrations of the stock solutions may be precisely as provided in Table 2, or may vary so long as the basal medium has one or more of the desirable properties described elsewhere herein, e.g., useful for low-stress culture of epithelial cells (e.g., 2-3 fold more growth of pre-stasis HMEC as compared to MCDB170 or WIT-P). For example, the final concentrations of the components in the stock solutions presented in Table 2 may independently vary (i.e., be greater than or less than) by 20% or less, 15% or less, 10% or less, 9% or less, 8% or less, 7% or less, 6% or less, 5% or less, 4% or less, 3% or less, 2% or less, or 1% or less, as compared to the final concentrations set forth in Table 2 of such components.

Stock A may be stored indefinitely in room temperature (RT). Stock B may be stored indefinitely in RT in a tightly closed plastic bottle. Stock C is dissolved in water with vigorous mechanical stirring plus mild heating as needed. It should not be boiled. It can be stored indefinitely in −20° C. or if sterilized, it can be stored at 4° C. for up to 2 months. Gentle heating and stirring may be required to redissolve some of its components before use.

Biotin and folinic acid are normally added to Stock D from more concentrated stock solutions. Concentration of pantothenic acid are expressed in terms of molar concentration of the Vitamin $B_5$. A formula weight based on one molecule of pantothenic acid plus one half atom of calcium has been used as the molecular weight. Stock D is stored in the dark at −20 C until used.

Stock G may be prepared fresh for each media prep because of the lability of the cysteine in solution and the narrow optimal range. It can be stored at −20° C. in the dark until use, but caution should be taken to ensure that there is no precipitate.

For stock H, aspartic and glutamic acid are added to slightly less than the final volume of water. One mL per liter of Stock A (phenol red) is added, and stock B (4N NaOH) is added with stirring just rapidly enough to keep the solution neutral (orange). When no solids remain and a stable orange color is achieved, alanine and glycine are dissolved and water is added to the final volume. If sterilized, Stock H can be stored in the dark at 4 C until use or it can be stored at −20 C indefinitely.

For stock I, adenine is dissolved in one half the final volume with the addition of 0.3 mL of stock B per 500 mL plus gentle warming. Lipoic acid is added from a more concentrated stock solution prepared by dissolving the solid in a few drop of Stock B followed by dilution with water. Putrescine is also added from a concentrated stock solution. myo-inositol and thymidine are dissolved in the final solution after it has been adjusted to volume by the addition of water. The solution is left alkaline and is stored in the dark at −20 C until use.

Stock J is stored at room temperature sterilized until use and added only just before the medium is to be used. The CaCl2 will precipitate if frozen. When added to the medium it is added slowly dropwise to a vigorously stirred solution.

Stock K1 is stored at RT sterilized until use and is added only on a final completion of the medium. The medium should not be refrozen after its addition.

For stock K2, one drop of concentrated HCl is added per liter. Solution K2 is stored sterile at room temperature. It must be discarded if it contains a precipitate or becomes orange colored. A yellow coloration to the filter used to sterilize the medium may indicate that the solution needs to be remade.

Because of the small amounts involved, Stock L is normally prepared from a series of more concentrated solutions, each containing one of the components at $1.0 \times 10^{-3}$ M. The Stock of the stannous chloride is prepared at $1.0 \times 10^4$ in 0.02N HCl to minimize precipitation on standing. Stock L is stored at RT sterilized at an acidic pH (1 drop of concentrated HCl added per liter).

Stock M is stored in the dark at −20 C until use. Small aliquots are made so that the solution is not thawed more than 5×.

Exemplary components added directly to the medium to make the complete media are given in the following table:

TABLE 3

| | Component | Molecular Weight | Final concentration (g/L, unless noted as mg) |
|---|---|---|---|
| Components added directly to medium | D-Glucose | 180.16 | 2.296 |
| | HEPES (Free Acid) | 238.3 | 5.361 |
| | KCl | 74.45 | 0.249 |
| | NaCl | 58.45 | 7.004 |
| | $KH_2PO_4$ | 136.09 | 0.034025 |
| | Sodium phoshate dibasic | | 0.035 g |
| | sodium phosphate monobasic | | 0.032 g |

TABLE 3-continued

| Component | Molecular Weight | Final concentration (g/L, unless noted as mg) |
|---|---|---|
| Ferric Nitrate | | .025 mg |
| Sodium Bicarbonate | | 0.6 |
| Thymidine | | .21883 mg |
| NaOH | | 0.32 g |
| linoleic acid | | .021 mg |
| Hypoxanthine NA | | 1.2 mg |

The above examples may be varied. For example, different stock solutions may be made with the total components subdivided into different subsets.

In conventional use, it is understood that one may add supplements to this media that are additionally required for long-term culture of their particular epithelial cell type of interest. The supplements may include glutamine, fetal bovine serum, bovine pituitary extract, insulin, isoproterenol, phenol red, hydrocortisone, apo-transferrin, oxytocin, cholera toxin, epidermal growth factor, β-estradiol, tri-iodo-thyronine, and AlbuMAx® albumin I.

As a further example, a complete medium with cholera toxin is listed below in Table 3A. This media may be termed M87A+CT+X Media for growth of pre-stasis HMEC. It contains basal medium plus albumin, cholera toxin, oxytocin and growth factor supplements. More details on the origin of and HMEC growth in this medium can be found in Garbe et al., Cancer Res 2009, and on our web site, hmec.lbl.gov. The medium contains a low level (0.25%) of serum.

To make 1000 ml of M87A+CT+X medium, one adds the following supplements to one 1 L of complete M87A media.

TABLE 3A

| Factor | Amount | Stock |
|---|---|---|
| Glutamine | 10.0 ml | 200 mM |
| Fetal bovine serum | 2.5 ml | n/a |
| Bovine pituitary extract | 2.5 ml | n/a |
| Insulin | 2.5 ml | 3 mg/ml |
| Isoproterenol | 1.0 ml | $5 \times 10^{-3}$M |
| Phenol red (only if using phenol red free basal media) | 0.4 ml | 0.5% |
| Hydrocortisone | 0.3 ml | 1 mg/ml |
| Apo-transferrin | 0.25 ml | 10 mg/ml |
| Oxytocin | 0.1 ml | 1 µM |
| Cholera toxin | 0.05 ml | 10 µg/ml |
| Epidermal growth factor | 0.05 ml | 100 µg/ml |
| β-estradiol | 0.025 ml | $2 \times 10^{-5}$M |
| Tri-iodo-thyronine | 0.025 ml | $2 \times 10^{-4}$M |
| Albumax I | 1.0 gm | n/a |

This is sterile filtered using a 0.2 µfilter unit with a PES (polyethersulfone). Albumax I can be added as a powder followed by filtration of the final medium or can be added as 10 ml of a 10% stock solution. The fetal calf serum can be ordered from Thermofisher-Gibco; cat #26140. The BPE can be ordered from Hammond Cell Tech cat #1078-NZ. Other sources are Lonza and BDBiosciences. The preferred insulin is Sigma cat #I5500 or BOC Sciences cat #11070-73-8. Isoproterenol can be obtained from Sigma, cat #I5627. Caution should be taken with the dust.

While the specific formulations given above are provided as examples for the culture of certain human mammary epithelial cells, it is understood that the formulations may be modified or adapted by one of ordinary skill in the art for application to a variety of different epithelial cell types and experimental protocols.

Also, if desired antibiotics may be used in the present media. This includes puromycin, hygromycin. G418, and blasticidin-S.

Example 3—Commonly Used Growth Media Causes Loss of Heterogeneity and Rapid Senescence in Primary Human Mammary Epithelial Cell Cultures Experimental examination of normal human mammary epithelial cell (HMEC) behavior, and how normal cells acquire abnormal properties, can be facilitated by in vitro culture systems that more accurately model in vivo biology. The breast consists of a complex admixture of many distinct cell types, e.g., epithelial, adipose, mesenchymal, endothelial. The epithelial cells are responsible for the differentiated mammary function of lactation, and are also the origin of the vast majority of human breast cancers. The mammary epithelium consists of at least two, broadly classified, lineages that arise from common progenitors: the luminal epithelial (LEP) and myoepithelial cell (MEP) lineages. Cultured HMEC have been employed in a variety of studies examining the normal processes governing growth, differentiation, self-organization, aging, and senescence, and how these normal processes are altered during immortal and malignant transformation. The effects of growth in the presence of extracellular matrix material, other cell types, and 3D culture can be compared with growth on plastic. Cultured HMEC, starting with normal cells, provide an experimentally tractable system to examine factors that may propel or prevent human aging and carcinogenesis. The growth media and methodology used to establish and maintain primary HMEC strains are crucial factors that directly impact the interpretation of cell biology experiments.

A cell culture media commonly used to support HMEC growth in vitro is the defined, MCDB170-type media developed by Ham and Stampfer in the 1980s, which has been available commercially for more than three decades (e.g. MEGM). Pre-stasis HMEC strains established in MCDB170-type media undergo a selection process usually within 2-4 passages, whereby a majority of primary HMEC in MCDB170-type media arrest in stasis due to stress, but some clones overcome stasis by epigenetic modification of p16. These post-selection post-stasis HMEC are sold commercially as "primary normal finite HMEC", however, based on protein and gene expression post-selection post-stasis HMEC do not express p16, are uniformly basal, and likely bear the closest relationship to metaplastic mammary tumors rather than normal epithelia. Defined WIT media was developed with the intent of enabling culture of normal and isogenic transformed HMEC, and the media was reported to better support the maintenance of LEP cells when combined with a proprietary tissue culture plastic (TCP), compared to MCDB170-type on standard TCP. Indeed, in the decades that MCDB170-type media has been in wide use, maintenance of cells with LEP phenotypes in culture beyond a couple of passages has been a persistent challenge, and WIT media partly addressed this issue. M85 and M87A media were created as lower-stress alternatives to MCDB170-type media, and support growth of HMEC as pre-stasis finite cells for up to 60 population doublings (PD), and maintain LEP for as many as 8 passages (roughly 30 PD). Starting from freshly isolated human mammary epithelial organoids most media are capable of supporting growth of multiple lineages for at least the first or second passage, however a rigorous comparison of media performance beyond the earliest stages is lacking.

Pre-stasis HMEC cultures starting from epithelial organoids have been examined, and inter-individual variation in the growth potential and heterogeneity was observed, with respect to epithelial lineages. In order to determine the impact of culture media on variation, the present study examined the phenotypes of pre-stasis HMEC cultures started from two different individuals, in three different culture media: MCDB170, WIT-P (on Primaria™ tissue culture plastic (TCP)), or M87A. The phenotypes (e.g. lineage marker expression, morphology, and growth) of cell strains were examined from passage 2 (p2) until they entered stress-induced senescence. M87A promoted 2-3 fold more growth of pre-stasis HMEC as compared to MCDB170 or WIT-P, which both caused the rapid onset of senescence. Growth rate, flow cytometry and immunofluorescence analyses of mammary epithelial lineage markers revealed pronounced differences in the abilities of the three different media to maintain HMEC lineages in a pre-stasis state. The ability to maintain lineage diversity is crucial for studying normal mammary epithelia as well as the process of malignant transformation.

Materials and Methods
Cell Culture

Human mammary epithelial cells (HMEC) from specimens 240 (Batch L) and 208 were obtained from reduction mammoplasty tissue of women aged 19 and 45 years, respectively. Both HMEC cultures were initiated in primary culture from organoids and grown up to senescence in serum-free containing WIT-P medium (Cellaria Biosciences), MCDB170 Medium (MEGM, Lonza, Walkersville, Md.), or serum containing media M87A. M87A is composed of 1:1 of DMEM/F12 and M171 (Thermofisher) supplemented with 0.5 ng/mL cholera toxin, 0.1 nM of oxytocin supplemented with 0.1% AlbuMAX I (Thermofisher) (Garbe et al., 2009).

Total population doublings (PD) were calculated beginning at passage 2 using the formula PD=log $2(N_{final}/N_{initial})$ is the number of cells counted during the initial seeding of each 10 cm tissue culture dish and the number of cells counted during sub-confluent levels. Each viable cell count was done in triplicates using a hemocytometer.

Immunofluorescence

Each HMEC strain was grown onto glass coverslips and fixed at their respective passages in 50% methanol and 50% acetone at −20° C. for 15 minutes. Following fixation, stored fixed HMEC were blocked in 1×PBS, 5% normal goat serum, and 0.1% Triton X-100 (Thermofisher) overnight. Each HMEC strain were stained with polyclonal rabbit Keratin 14 (1:1000, Covance PRB-155P), and Keratin 19 (1:100, Thermofisher) in blocking buffer and incubated in 4° C. overnight. Following 3 washes in 1×PBS, each fixed HMEC were incubated with fluorescent secondary antibodies for 2 hours at room temperature with 1:200 Alexa Fluor 488 Rat anti-Mouse IgG2 and 1:200 Alexa Fluor 568 and DAPI. Cells were imaged using Zeiss LSM710 confocal microscope. Marker-based watershed segmentation was performed as previously described (MatLab, Mathworks Inc).

Immunohistochemistry

Cells were washed twice with PBS and fixed for 30 min with 4% paraformaldehyde. Cells were permeabilized with 0.1% Triton X-100 for 5 min, blocked for 30 min in PBS containing 5% normal goat serum, and incubated with p16 antibody (Santa Cruz Biotech, SC-56330, clone JC8) for 60 min. Antibody binding was visualized using peroxidase mouse ABC kit and DAB substrate kit (Vector Labs, Burlingame, Calif.).

Flow Cytometry

Subconfluent cells were trypsinized, harvested and fixed in 2% paraformaldehyde. Cells were blocked in FACS buffer and stained with CD227-FITC (BD, clone HMPV, 1:50) and CD10-PE (BioLegend, clone HI10a, 1:100) were added to cells in buffer for 25 mins protected from light and on ice, washed in PBS, and analyzed using FACS Calibur (Becton Dickinson). FlowJo X was used to for computer analysis.

Results
Growth Rates and Senescence

To determine the impact of cell culture media on growth characteristics of pre-stasis HMEC, organoids from two women were used to generate pre-stasis strains in three different culture media: M87A, MCDB170, and WIT-P. Growth curves were generated starting with p2 cells from both individuals. Specimens 240 L (FIG. 1, panel A) and 208 (FIG. 1, panel B) were from discarded reduction mammoplasty tissue from women aged 19 and 45 years, respectively. Cells in M87A or MCDB170 media were grown on standard tissue culture plastic (TSP) dishes, whereas cells in WIT-P were grown on Primaria™ dishes. HMEC in WIT-P appeared large and vacuolated as early as p3, and the entire cultures stopped growth by p'7-p8. A majority of 240 L HMEC in MCDB170 entered senescence as early as p3, but clones of post-stasis cells exhibited some additional growth after ~60 days, which ceased growth by 7p. Clonal outgrowth of post-stasis cells is a common consequence of growing pre-stasis HMEC in high stress conditions. Specimen 208 in MCDB170 ceased all growth by p9, but the emergence of post-stasis cells was not observed even after waiting an additional 60 days. In M87A media, 240 L stopped growth at p16 and 208 stopped at p11. Morphological differences between cells grown in the different media were visible as early as p3, such as large and vacuolated cells consistent with senescence phenotypes in MCDB170 and WIT-P compared to M87A, which become pronounced by p4. Expression of $p16^{INK4A}$ protein was detected in most cells by p4 in WIT-P and MCDB170 media, whereas little p16 was detected in p4 M87A cultures (FIG. 1, panels C and D). M87A supported superior growth of pre-stasis HMEC compared to WIT-P and MCBD170 media, which both cause rapid induction of stress associated stasis.

Maintenance of Epithelial Lineage Diversity

Figure 2:
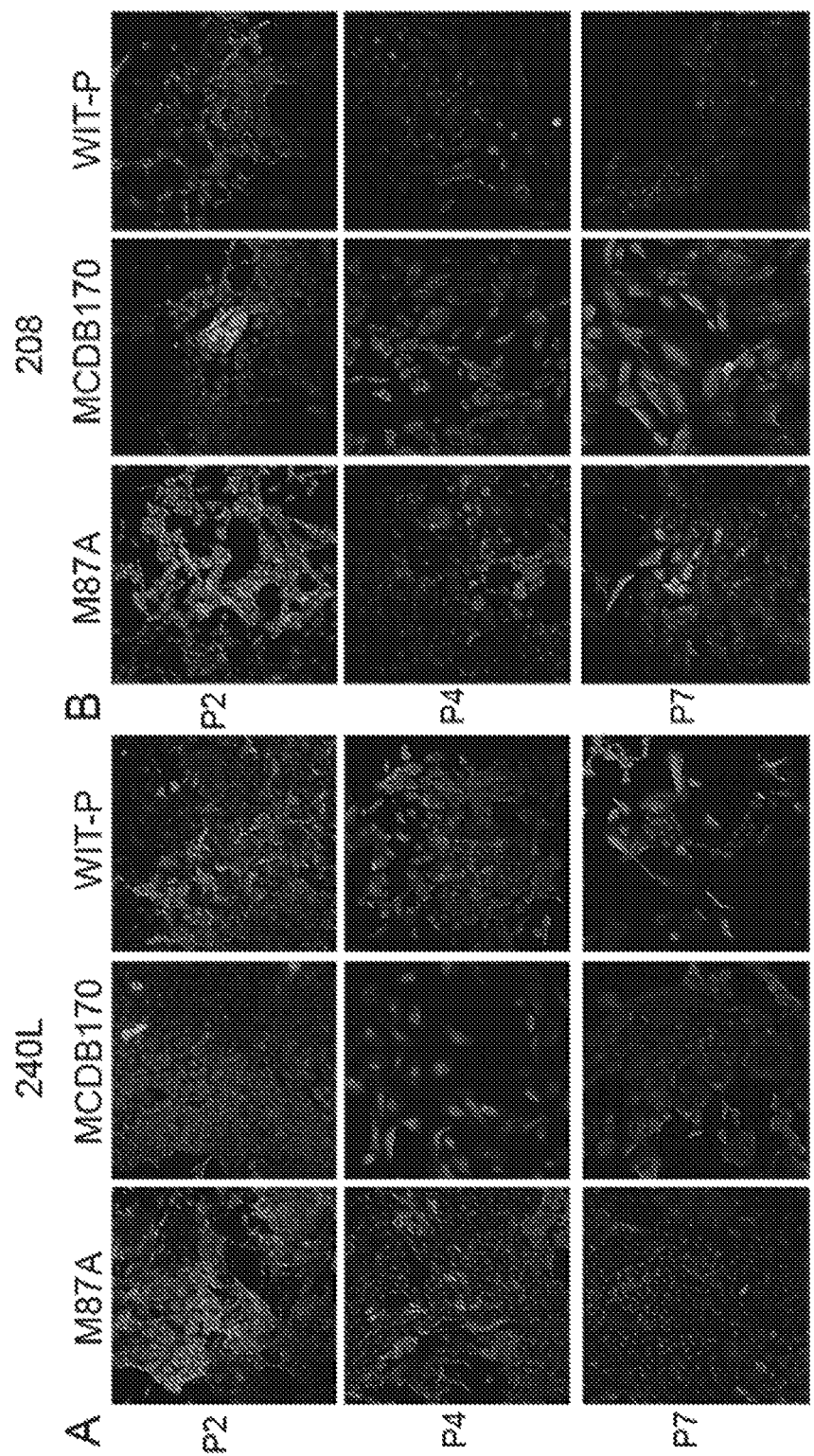
FIG. 2 shows immunofluorescence assessment of epithelial lineages in pre-stasis HMEC cultures. Cultures established from specimens (A) 240 L and (B) 208 were stained to detect expression of (K)eratin 14, K19, and DAPI by immunofluorescence. Representative images are shown from passage 2, 4, and 7 HMEC grown in M87A, MCDB170, and WIT-P media. Magnification bars represent 20 μm.
Figure 3:
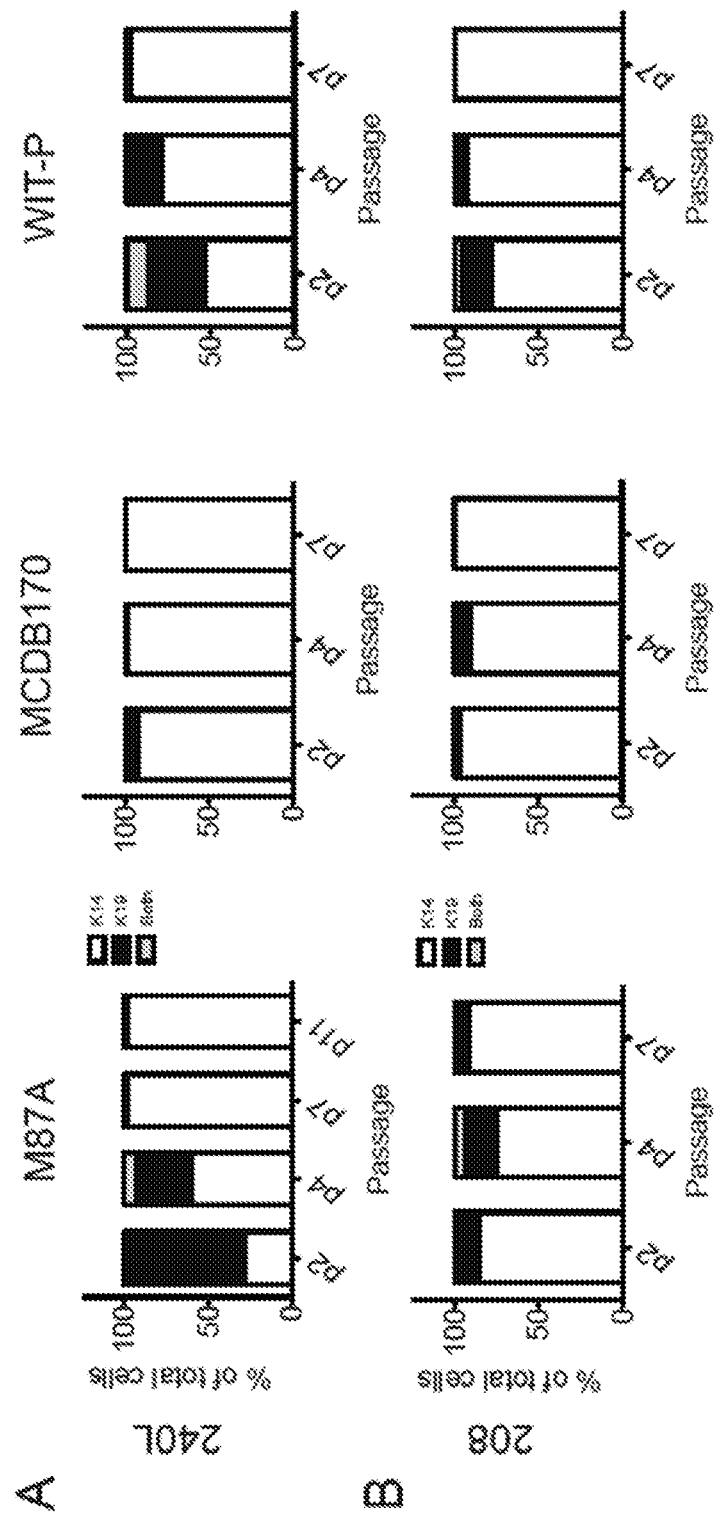
FIG. 3 shows low stress M87A maintains lineage heterogeneity in pre-stasis HMEC strains. Panels A and B: Bar graphs showing the proportions of K14+ MEP, K19+ LEP, or K14+/K19+ cells in cultures of specimen 240 L (panel A), and 208 (panel B), as determined with automated marker-based watershed cell segmentation from 2 replicates and 10 images from each culture condition. Panels C and D: Bar graphs showing the proportion of CD227+ LEP as a percentage of total cells in cultures from specimen 240 L (panel C), and 208 (panel D). Data were derived from flow cytometry analysis of CD227 and CD10 expression of the pre-stasis cultures over passage, in M87A, WIT-P, and MCDB170. Panels E and F: Filled line plots of the Shannon Diversity Index as a function of passage for specimens 240 L (panel E) and 208 (panel F) cultured in M87A, WIT-P, and MCDB170. Values closest to 1.0 denote the most diversity.
Figure 3:
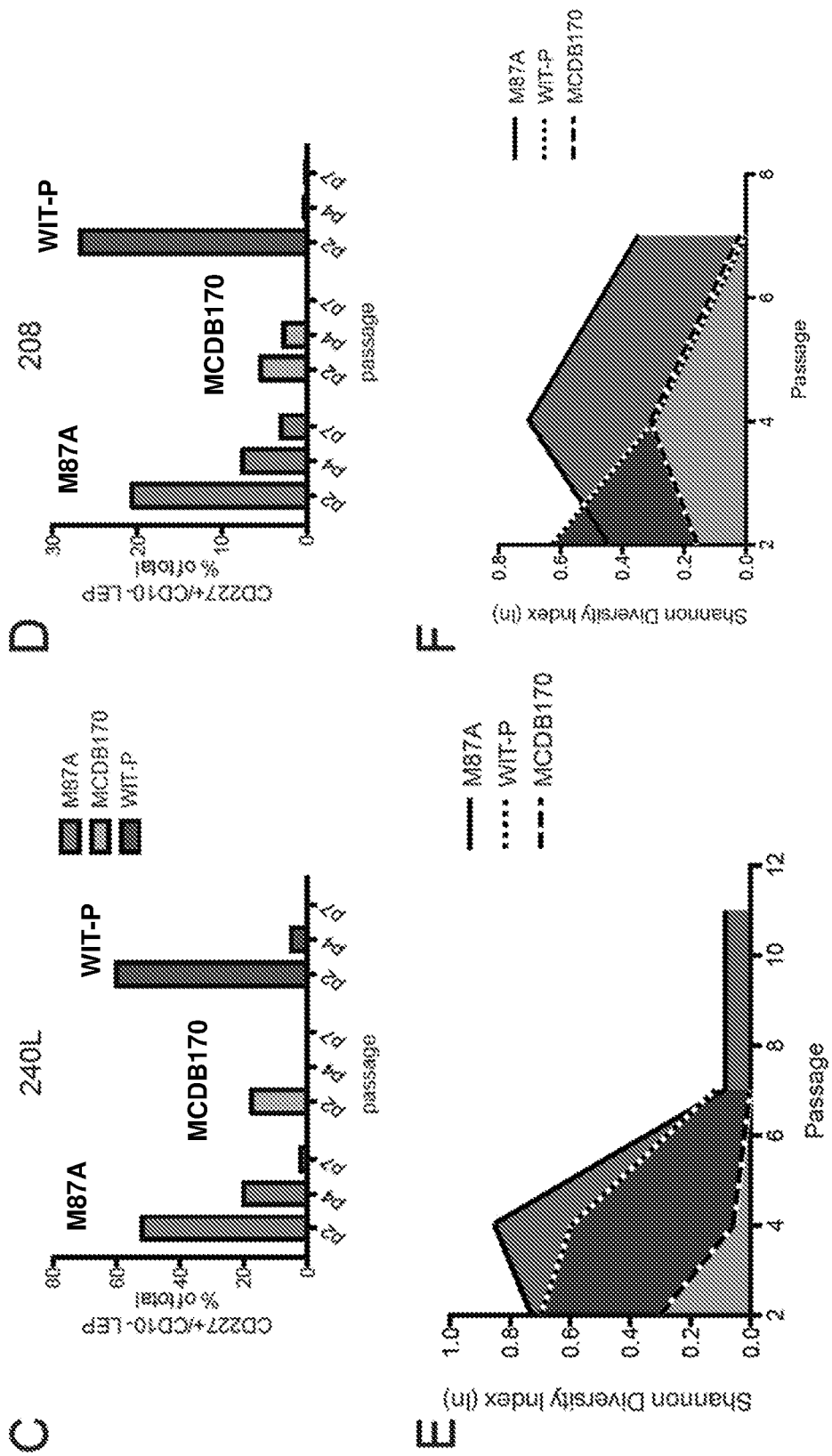

Maintaining the different epithelial lineages observed in vivo also in culture is essential to understanding how the epithelium functions normally, and which cell types are actually impacted by pathological changes. Cultures were examined by immunofluorescence for keratin (K)14 and K19 expression (FIG. 2, panels A and B), and by FACS for CD227 (Sialomucin1) and CD10 (CALLA) to assess lineage heterogeneity as a function of passage. K14 and CD10 are conventionally used as biomarkers of myoepithelial cells, and K19 and CD227 are biomarkers of luminal cells. Immunofluorescence images showed that both luminal and myoepithelial cells were present at p2 in all conditions, but that luminal cells rapidly disappeared in MCDB170 and WIT-P. Marker-based watershed segmentation was used to quantify the fluorescence images. Cultures of both 240 L and 208 in M87A contained cells from both lineages for more than 7 passages, with the luminal cells decreasing proportionately with successive passages. HMEC grown in WIT-P had a large proportion of luminal cells at p2, some large and flat K19-expressing cells remained at p4, and none remained by p7. Cultures maintained in MCDB170 had lost nearly all luminal cells by p2 (FIG. 3, panels A and B). Flow cytometry analyses of CD227 and CD10 revealed the same pattern: CD227+ luminal cell were maintained at a higher proportion and for more passages in M87A compared to MCDB170 or WIT-P (FIG. 3, panels C and D). To quantify the heterogeneity of the cultures with respect to lineage, Shannon Diversity Indexes were calculated as a function of passage. Comparison of the area under the curves demonstrates that M87A media maintained heterogeneity longer compared to WIT-P and MCDB170 (FIG. 3, panels E and F).

Defined Versus Serum-Containing M87A Formulation

Figure 4:
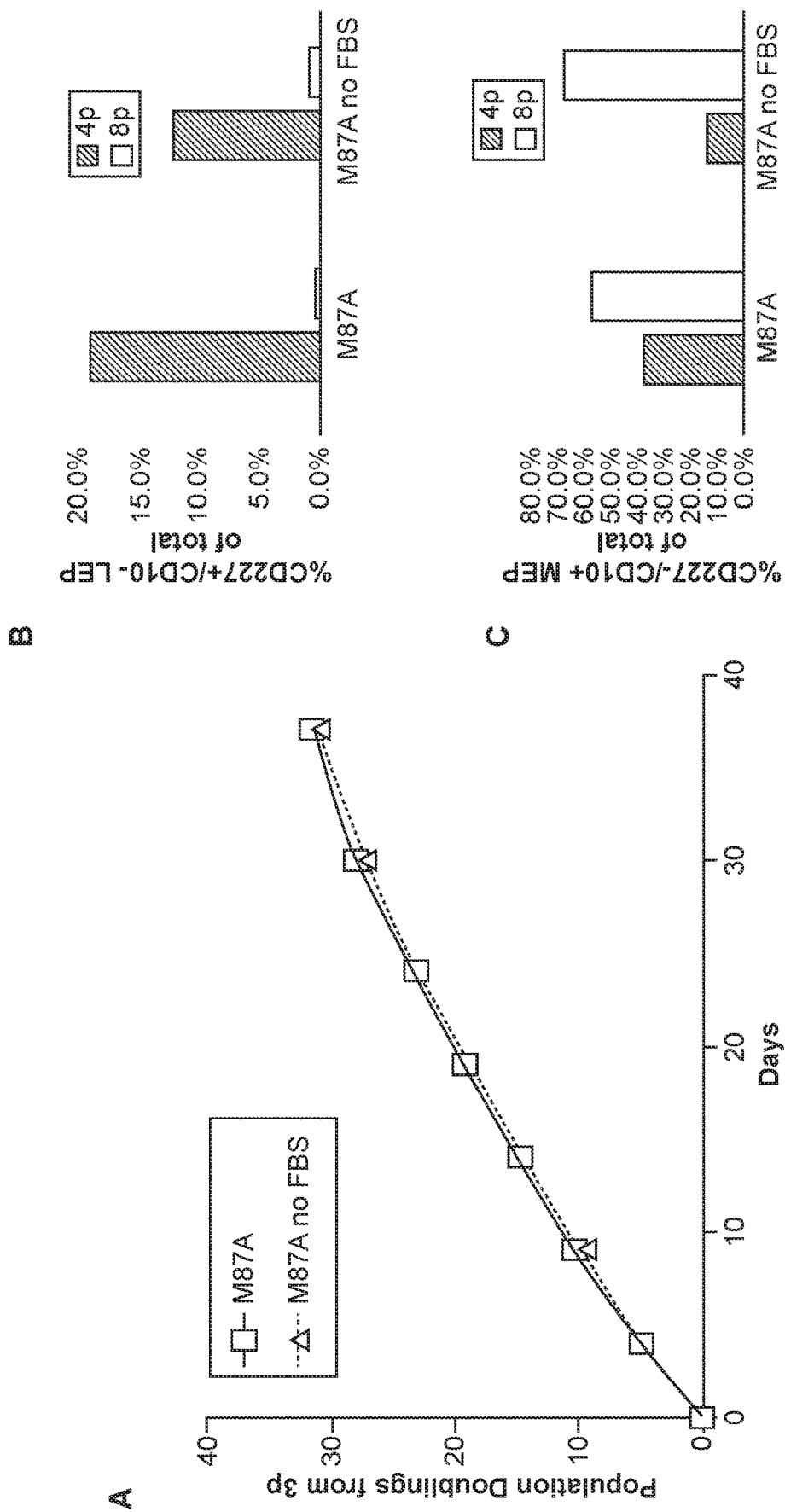
FIG. 4 provides data relating to luminal cells in M87A plus supplements ("M87A") without fetal bovine serum. Panel A: Curves showing population doublings as a function of time in days for 240 L grown in M87A plus supplements ("M87A") with and without 0.25% FBS from 3p. Growth rates were only assessed to 10p, thus the curves to not reflect cultures reaching stasis. Bar graphs showing the proportion of CD227+ LEP (panel B) and CD10+ MEP (panel C) as a percentage of total cells in cultures grown with or without FBS.

One perceived advantage of WIT-P and MCDB170 is that they are defined media, with exception of the bovine pituitary extract component in MCDB170, which is thought to offer some advantages over serum containing media because the composition is less variable between batches. M87A normally has 0.25% fetal bovine serum (FBS). Growth curves performed from p3 with 240 L showed no difference in growth rates between serum-containing or serum-free M87A (FIG. 4, panel A). However, flow cytometry analysis of CD227 and CD10 expression revealed that in serum-free M87A there was nearly 30% fewer CD227+/CD10− luminal cells at p4, and over 50% fewer CD227−/CD10+ MEP present at p4, compared to serum-containing M87A (FIG. 4, panels B and C). These results suggest that FBS is not an essential media component, but it may be a component that fosters differentiation into more mature luminal and myoepithelial cell types.

Discussion

In order to use cell culture as a system to enable study of human tissues, the culture systems must be able to support the multiple types of cells present in the native tissue. In the present study, these are human mammary epithelia. When using a single culture media, inter-individual variation is readily apparent in pre-stasis HMEC cell cultures. Within the breast cancer and mammary biology literature there is some disagreement between labs that use different cell culture methods. Described here is the impact of three different cell culture media on variation within pre-stasis HMEC cultures that were derived from reduction mammoplasty tissues of two different individuals. MCDB170-type and WIT-P, the most commonly used and commercially available media, caused rapid stress-induced stasis and loss of lineage diversity, and in one case caused emergence of post-selection post-stasis cells. M87A outperformed both of the defined media in total PD and maintained lineage diversity for as many as 30 PD. In addition, M87A performed well without serum, exhibiting reduced diversity, but maintaining population doublings and growth rate comparable to the fully supplemented M87A.

MCDB170 media is the prototype defined media, upon which MEGM and other commonly used HMEC growth media are based. In the original publication of MCDB170, rapid clonal growth was followed for only 10 days and, at that time, it was considered the superior media compared to predecessors such as MM. In that first description of MCDB170 media, a lag in growth at passages 2-4 was reported that was thought to be a form of selection, because the vast majority of cells underwent senescence and only clones of finite lifespan cells emerged. Sixteen years later it was discovered that the cells emerging from the 20- to 40-day-long lag phase had silenced p16, and were termed post-selection post-stasis HMEC (or vHMEC). There is not a known counterpart to these post-selection post-stasis cells in vivo, but there is some resemblance to rare metaplastic breast tumors. Interestingly, these cells have been commercially available as "normal primary HMEC" for more than two decades. Upon further reflection, defined media like MCDB170, which was optimized for clonal growth, not mass culture, may inflict significant stress on the cells that causes a majority to rapidly enter stasis, but also enables clones to undergo selection and grow out.

The WIT-P media is also defined, and was intended to enable better growth of the luminal epithelial lineage. Representation of K19+/K14− and CD227+/CD10− luminal epithelial cells in WIT-P and at p2 that was comparable to M87A was observed, but the luminal were lost as early as p3 in WIT-P. In the present study, growth of both specimens was better in WIT-P than in MCDB170, and the appearance of post-stasis cells in WIT-P was not observed. However, in the original description of WIT media, the reported growth curve shows a 20-40 day-long lag in growth, which would be consistent with cultures going through selection. The early loss of the luminal cells, and the early appearance of large vacuolated cells, was likely due to stress. The composition of WIT-P is proprietary, thus the factors likely to cause the stress are unknown.

In the case of all three media that were compared in the present study, non-dissociated epithelial organoids were used to initiate the pre-stasis cultures. After the organoids attached to TCP, subsequent sub-cultures were comprised of partially trypsinized cells that had migrated out of the epithelial structures. Dissociation of organoids prior to plating causes a rapid change in microenvironment and a mechanically and chemically stressful environment. The organoid attachment method enables the establishment of ensemble cultures consisting of luminal, myoepithelial, and progenitor cells, which we speculate is important for the stochastic creation of an ecology that supports multiple epithelial cell types. M87A was developed with the goal of reducing stress in HMEC mass cultures. In this regard, the hormone oxytocin is one of the key media additives, because in addition to its well-known roles in maternal, emotional, and sexual behaviors, it also protects cells from death due to metabolic stress. In the mammary gland, myoepithelial cells express the oxytocin receptor, and it is possible that the oxytocin component indirectly supports luminal cells by acting directly upon the cultured myoepithelial cells.

Defined media are created for the purpose of eliminating variability and unknown components that are introduced by animal sera. Both WIT-P and MCDB170 are serum free, whereas M87A normally has 0.25% fetal calf serum (FCS). Withdrawal of the FCS component from M87A did not alter the growth rate of HMEC from 3p to 10p, but there was a noticeable drop in differentiated luminal and myoepithelial cells. The activity of FCS in HMEC cultures is not well defined, however, it may impact differentiation more than growth. Gudjonsson et al. used this to advantage in order to increase the likelihood of transducing mammary progenitor cells with a type-C retrovirus, which can only transduce proliferating cell types. Addition of FCS into H14 media hastened differentiation of mammary epithelial cells into more terminal states, thus leaving progenitor cells as the only ones still dividing. The outcome was the D492 cell line, which is heterogeneous with respect to lineage, and contains multi-potent progenitors. The recent report of conditions for isolating and maintaining estrogen receptor (ER)-expressing pre-stasis luminal cells in HMEC cultures also used serum to advantage. That method relied upon establishing HMEC cultures from dissociated epithelial organoids in FAD media, which contains 5% FCS, and to two different TGF-beta inhibitors. ER+ luminal cells tend to be more observable in 3-D cultures of pre-stasis HMEC in M87A, whereas ER stains only weakly in pre-stasis cells on TCP. ER+ luminal cells could be isolated from cells that migrated from attached organoids in FAD media, so dissociation is not a requirement, but seemingly the media is a requirement.

Cell culture models lack a microenvironmental context, but the methods and type of media used also can significantly alter the cell intrinsic biology in a detrimental manner. Combining media that can maintain in vitro the multiple types of cells that comprise a tissue in vivo is a good starting place. Then combining optimal media and culture methodologies with new technologies such as microphysiological systems are likely to give rise to new and accurate human tissue model systems.

Example 4: Comparative Example—Basal Medium Derived from Mixture of Media

As a comparative example, a 1:1 mixture of commercially available DMEM/F12 and MEBM or M171 (or other MCDB170-type media) was prepared. Details on MEBM and M171 may be found as referenced above.

A composition of DMEM/F12 is provided in the following table:

TABLE 4

| Components | Molecular Weight | Concentration (mg/L) | mM |
|---|---|---|---|
| Amino Acids | | | |
| Glycine | 75 | 18.75 | 0.25 |
| L-Alanine | 89 | 4.45 | 0.049999997 |
| L-Arginine hydrochloride | 211 | 147.5 | 0.69905216 |
| L-Asparagine-H2O | 150 | 7.5 | 0.05 |
| L-Aspartic acid | 133 | 6.65 | 0.05 |
| L-Cysteine hydrochloride-H2O | 176 | 17.56 | 0.09977272 |
| L-Cystine 2HCl | 313 | 31.29 | 0.09996805 |
| L-Glutamic Acid | 147 | 7.35 | 0.05 |
| L-Glutamine | 146 | 365 | 2.5 |
| L-Histidine hydrochloride-H2O | 210 | 31.48 | 0.14990476 |
| L-Isoleucine | 131 | 54.47 | 0.41580153 |
| L-Leucine | 131 | 59.05 | 0.45076334 |
| L-Lysine hydrochloride | 183 | 91.25 | 0.4986339 |
| L-Methionine | 149 | 17.24 | 0.11570469 |
| L-Phenylalanine | 165 | 35.48 | 0.2150303 |
| L-Proline | 115 | 17.25 | 0.15 |
| L-Serine | 105 | 26.25 | 0.25 |
| L-Threonine | 119 | 53.45 | 0.44915968 |
| L-Tryptophan | 204 | 9.02 | 0.04421569 |
| L-Tyrosine disodium salt dihydrate | 261 | 55.79 | 0.21375479 |
| L-Valine | 117 | 52.85 | 0.4517094 |
| Vitamins | | | |
| Biotin | 244 | 0.0035 | 1.43E−05 |
| Choline chloride | 140 | 8.98 | 0.06414285 |
| D-Calcium pantothenate | 477 | 2.24 | 0.004696017 |
| Folic Acid | 441 | 2.65 | 0.006009071 |
| Niacinamide | 122 | 2.02 | 0.016557377 |
| Pyridoxine hydrochloride | 206 | 2 | 0.009708738 |
| Riboflavin | 376 | 0.219 | 5.82E−04 |
| Thiamine hydrochloride | 337 | 2.17 | 0.006439169 |
| Vitamin B12 | 1355 | 0.68 | 5.02E−04 |
| i-Inositol | 180 | 12.6 | 0.07 |
| Inorganic Salts | | | |
| Calcium Chloride (CaCl2) (anhyd.) | 111 | 116.6 | 1.0504504 |
| Cupric sulfate (CuSO4—5H2O) | 250 | 0.0013 | 5.20E−06 |
| Ferric Nitrate (Fe(NO3)3 9H2O) | 404 | 0.05 | 1.24E−04 |
| Ferric sulfate (FeSO4—7H2O) | 278 | 0.417 | 0.0015 |
| Magnesium Chloride (anhydrous) | 95 | 28.64 | 0.30147368 |
| Magnesium Sulfate (MgSO4) (anhyd.) | 120 | 48.84 | 0.407 |
| Potassium Chloride (KCl) | 75 | 311.8 | 4.1573334 |
| Sodium Bicarbonate (NaHCO3) | 84 | 1200 | 14.285714 |
| Sodium Chloride (NaCl) | 58 | 6995.5 | 120.61207 |
| Sodium Phosphate dibasic (Na2HPO4) anhydrous | 142 | 71.02 | 0.50014085 |
| Sodium Phosphate monobasic (NaH2PO4—H2O) | 138 | 62.5 | 0.45289856 |
| Zinc sulfate (ZnSO4—7H2O) | 288 | 0.432 | 0.0015 |
| Other Components | | | |
| D-Glucose (Dextrose) | 180 | 3151 | 17.505556 |
| HEPES | 238 | 3574.5 | 15.018908 |
| Hypoxanthine Na | 159 | 2.39 | 0.015031448 |
| Linoleic Acid | 280 | 0.042 | 1.50E−04 |
| Lipoic Acid | 206 | 0.105 | 5.10E−04 |
| Putrescine 2HCl | 161 | 0.081 | 5.03E−04 |
| Sodium Pyruvate | 110 | 55 | 0.5 |
| Thymidine | 242 | 0.365 | 0.001508265 |

A composition of MCDB170 is provided in the following table:

TABLE 5

| Component | concentration (M) | mg/L |
|---|---|---|
| Amino Acids | | |
| Glycine | 1.00E−04 | 7.507 |
| L-Alanine | 1.00E−04 | 8.909 |
| L-Arginine | 1.00E−04 | 63.21 |
| L-Asparagine H2O | 1.00E−03 | 150.1 |
| L-Aspartic acid | 1.00E−04 | 13.31 |
| L-Cysteine HCl H2O | 7.00E−05 | 12.29 |
| L-Glutamic acid | 1.00E−04 | 14.71 |
| L-Glutamine | 2.00E−03 | 292.2 |
| L-Histidine HCl H2O | 1.00E−04 | 20.97 |
| L-Isoleucine | 1.00E−04 | 13.12 |
| L-Leucine | 3.00E−04 | 39.36 |
| L-Lysine HCl | 2.00E−04 | 36.54 |
| L-Methionine | 3.00E−05 | 4.476 |
| L-Phenylalanine | 3.00E−05 | 4.956 |
| L-Proline | 5.00E−05 | 5.755 |
| L-Serine | 3.00E−04 | 31.53 |
| L-Threonine | 3.00E−04 | 35.73 |
| L-Tryptophan | 3.00E−05 | 6.126 |
| L-Tyrosine | 5.00E−05 | 9.06 |
| L-Valine | 3.00E−04 | 35.16 |
| Vitamins | | |
| d-Biotin | 3.00E−08 | 0.007329 |
| Folinate Ca 5H2O | 1.00E−08 | 0.006016 |
| DL-alpha-Lipoic acid | 1.00E−08 | 0.002063 |
| Niacinamide | 5.00E−05 | 6.105 |
| D-Pantothenate 1/2 Ca | 1.00E−06 | 0.2383 |
| Pyridoxine HCl | 3.00E−07 | 0.06168 |
| Riboflavin | 3.00E−07 | 0.1129 |
| Thiamin HCl | 1.00E−06 | 0.3373 |
| Vitamin B12 | 1.00E−07 | 0.1355 |
| Trace Elements | | |
| CuSO4 5H2O | 1.00E−09 | 0.0002497 |
| FeSO4 7H2O | 5.00E−06 | 1.39 |
| H2SeO3 | 3.00E−08 | 0.003869 |
| MnSO4 5H2O | 5.00E−10 | 0.0001205 |

TABLE 5-continued

| Component | concentration (M) | mg/L |
|---|---|---|
| $Na_2SiO_3\ 9H_2O$ | 5.00E−07 | 0.1421 |
| $(NH_4)6Mo_7O_{24}\ 4H_2O$ | 1.00E−09 | 0.001236 |
| $NH_4VO_3$ | 5.00E−09 | 0.000585 |
| $NiCl_2\ 6H_2O$ | 5.00E−12 | 0.000001189 |
| $SnCl_2\ 2H_2O$ | 5.00E−12 | 0.000001128 |
| $ZnSO_4\ 7H_2O$ | 5.00E−07 | 0.1438 |
| Other Organic | | |
| Adenine | 1.00E−06 | 0.1351 |
| Choline Chloride | 1.00E−04 | 13.96 |
| D-Glucose | 8.00E−03 | 1441.3 |
| myo-Inositol | 1.00E−04 | 18.02 |
| Putrescine 2HCl | 1.00E−09 | 0.0001611 |
| Sodium Pyruvate | 1.00E−03 | 110 |
| Thymidine | 3.00E−07 | 0.07266 |
| Bulk inorganic ions | | |
| $CaCl_2\ 2H_2O$ | 2.00E−03 | 294 |
| KCl | 2.50E−03 | 186.4 |
| $MgSO_4\ 7H_2O$ | 1.50E−03 | 396.6 |
| NaCl | 1.20E−01 | 7014 |
| $KH_2PO_4$ | 5.00E−04 | 68.05 |
| Miscellaneous | | |
| HEPES (free acid) | 3.00E−02 | 7149 |
| NaOH | 1.60E−02 | 640.2 |
| Phenol Red | 3.30E−06 | 1.242 |

In Table 5 above, it is noted that the pH of the medium is 7.6 at 22° C. and the osmolality is 300 milliosmoles. The molarity listed for "D-Pantothenate ½ Ca" is for pantothenate ion, and the molarity of molybdenum is 7.0E-09 M. Further, the NaOH is used to adjust pH, so the exact amount will vary. The final pH at 37 C and 5% $CO_2$ is 7.3-7.4.

Example 5: Comparison of M87A Basal Medium with Basal Medium Derived from Mixture of Media M87A basal medium was prepared as described above in Example 2. Basal medium was also prepared by a 1:1 mixture of commercially available media, as described in Example 4 (M171 or MEGM mixed with DMEM/F12 at a 1:1 ratio). The two prepared media were compared as to their ability to support growth of normal human mammary epithelial cells. The M87A basal medium plus supplements supported identical or better growth—as determined by rate and morphological features—compared to the media generated from commercially available media.

Figure 5:
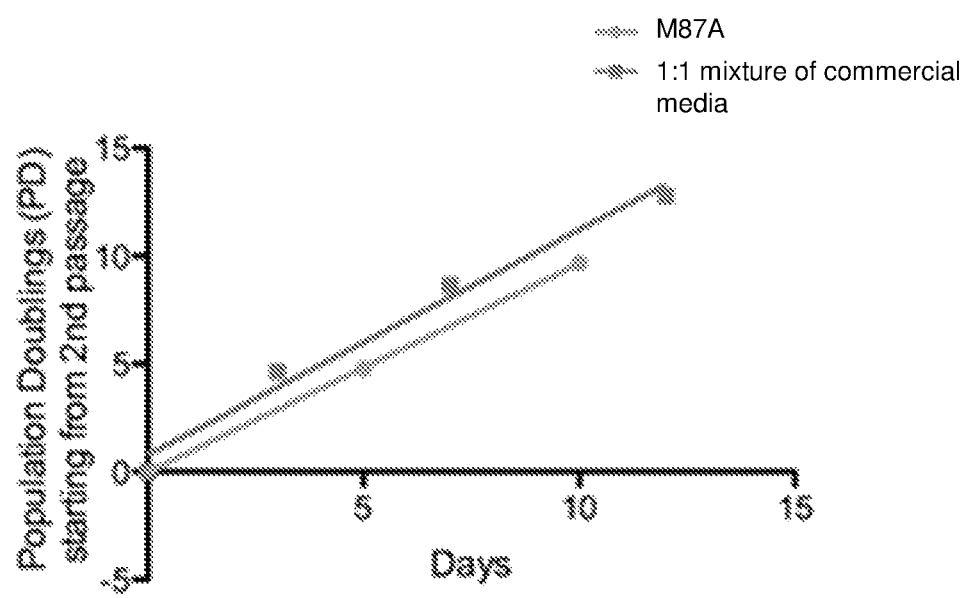
FIG. 5 is a line graph showing a comparison of HMEC growth curves in M87A plus supplements ("M87A") (circles) versus a mixture of commercially obtained media (squares), using an HMEC strain established from specimen 259P.

Representative growth data for HMEC are shown in FIG. 5. The data were obtained with an HMEC strain established from specimen 259P, who was age 49 at the time of surgery. 150 μm organoids from the specimen were cultured side-by-side in the two types of prepared media. Growth curves are shown as, and slopes were calculated as, population doublings per day. The graph shows that the slopes of the growth curves are very similar in the M87A basal medium plus supplements (circles) versus the mixture of commercially obtained media (squares) over 3-4 passages beginning at passage 2. The slope of the growth curve was 0.9670±0.006351 for the M87A basal medium plus supplements, and was 1.044±0.1025 for the mixture of commercial media.

Notwithstanding the appended clauses, the disclosure set forth herein is also defined by the following clauses:
1. A combination of defined stock solutions for making a basal medium, useful for low stress culture of normal human epithelial cells, comprising:
   (a) a solution of 20 naturally occurring amino acids;
   (b) a solution of vitamins including folic acid;
   (c) a solution of trace elements including calcium chloride;
   (d) a solution comprising adenine, choline chloride, D-glucose myo-inositol, putrescine 2HCl, sodium pyruvate, and thymidine; and
   (e) a solution of HEPES buffer, NaOH, D-glucose and phenol red (optional),
   wherein the defined stock solutions (a) through (e) are suitable for combination into the basal medium.
2. A basal medium consisting essentially of stock solutions (a) though (e) in clause 1.
3. A basal medium comprising:
   (a) 20 naturally occurring amino acids, including L-arginine hydrochloride in an amount between 90 and 120 mg/L;
   (b) vitamins including folic acid in an amount of between 1 and 1.5 mg/L;
   (c) trace elements including calcium chloride in an amount between 190 and 220 mg/L;
   (d) other organics, including adenine, choline chloride, D-glucose (1700-2500 mg/L), myo-inositol, putrescine 2HCl. sodium pyruvate, and thymidine; and
   (e) HEPES buffer, NaOH, D-glucose (1000-2000 mg/L) and phenol red (optional), provided that values given in mg/L are mg in distilled water and may be varied by plus or minus an insignificant amount, e.g. 5%, 10%, 15% or 20%, on a component or component basis (e.g., a component by component basis).
4. The basal medium of clause 3 containing the components as defined in Table 1, with the proviso that phenol red is an optional ingredient.
5. An optimized medium containing the basal medium of clause 2 and further comprising serum and a growth factor.
6. The medium of one of clauses 2-5 free of conditioned medium.
7. A method of preparing the basal medium of clause 1, comprising the step of preparing solutions of elements (a) through (e) separately and combining individually as separate stock solutions.
8. A method for culturing normal human epithelial cells, comprising the step of culturing the normal human epithelial cells with a culture medium comprising a basal medium as defined in one of clauses 2-6, for a period of time over which at least 10 doubling of the normal human epithelial cells occurs during the culturing.
9. The method of clause 8 wherein the cells are mammary cells.

Notwithstanding the appended clauses and the clauses above, the disclosure set forth herein is also defined by the following clauses:
1. A combination of defined stock solutions for making a basal medium, useful for low stress culture of normal human epithelial cells, comprising:
   (a) a solution of 20 naturally occurring amino acids;
   (b) a solution of vitamins including folic acid;
   (c) a solution of trace elements including calcium chloride;
   (d) a solution comprising adenine, choline chloride, D-glucose myo-inositol, putrescine 2HCl, sodium pyruvate, and thymidine; and
   (e) a solution of HEPES buffer, NaOH, and D-glucose, wherein the defined stock solutions (a) through (e) are suitable for combination into the basal medium.

2. The combination of defined stock solutions of clause 1, wherein the solution of HEPES buffer, NaOH, and D-glucose further comprises phenol red.
3. A basal medium comprising a mixture of stock solutions (a) through (e) as set forth in clause 1 or clause 2.
4. A basal medium consisting essentially of a mixture of stock solutions (a) through (e) as set forth in clause 1 or clause 2.
5. An optimized cell culture medium, comprising:
   the basal medium of clause 3 or clause 4; and
   serum, a growth factor, or both.
6. The optimized medium of clause 5, comprising serum and a growth factor.
7. A method of making a basal medium useful for low stress culture of epithelial cells, comprising combining:
   (a) a solution of 20 naturally occurring amino acids;
   (b) a solution of vitamins including folic acid;
   (c) a solution of trace elements including calcium chloride;
   (d) a solution comprising adenine, choline chloride, D-glucose myo-inositol, putrescine 2HCl, sodium pyruvate, and thymidine; and
   (e) a solution of HEPES buffer, NaOH, and D-glucose, in a container to produce a mixture of a basal medium useful for low stress culture of epithelial cells.
8. The method according to clause 7, further comprising, prior to the combining, preparing solutions (a) to (e) separately.
9. The method according to clause 7 or clause 8, wherein the solution of HEPES buffer, NaOH, and D-glucose further comprises phenol red.
10. The method according to any one of clauses 7 to 9, further comprising, after the combining, sterilizing the basal medium.
11. The method according to any one of clauses 7 to 10, further comprising, after the combining, culturing epithelial cells in a medium comprising the basal medium.
12. The method according to any one of clauses 7 to 11, wherein the epithelial cells are normal epithelial cells.
13. The method according to any one of clauses 7 to 12, wherein the epithelial cells are human mammary epithelial cells (HMEC).
14. A basal medium comprising:
   (a) 20 naturally occurring amino acids, including L-arginine hydrochloride in an amount between 90 and 120 mg/L;
   (b) vitamins including folic acid in an amount of between 1 and 1.5 mg/L;
   (c) trace elements including calcium chloride in an amount between 190 and 220 mg/L;
   (d) other organics, including adenine, choline chloride, D-glucose (1700-2500 mg/L), myo-inositol, putrescine 2HCl. sodium pyruvate, and thymidine; and
   (e) HEPES buffer, NaOH, and D-glucose (1000-2000 mg/L), provided that values given in mg/L are mg in distilled water and may be varied by plus or minus an insignificant amount, e.g. 5%, 10%, 15% or 20%, on a component by component basis.
15. The basal medium of Clause 14, wherein the solution of HEPES buffer, NaOH, and D-glucose (1000-2000 mg/L) further comprises phenol red.
16. The basal medium of clause 14 comprising the components as defined in Table 1, with the proviso that phenol red is an optional ingredient.
17. A medium of any one of clauses 3 to 6 or 14 to 16, wherein the medium is free of conditioned medium.
18. A method for culturing epithelial cells, comprising the step of culturing the normal human epithelial cells with a culture medium comprising a medium as defined in any one of clauses 3 to 6 or 14 to 17, for a period of time over which at least 10 population doublings of the epithelial cells occurs during the culturing.
19. The method according to clause 18, wherein the epithelial cells are normal epithelial cells.
20. The method according to clause 18 or clause 19, wherein the epithelial cells are human mammary epithelial cells (HMEC).

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

What is claimed is:

1. A basal medium, useful for low stress culture of normal human mammary epithelial cells (HMECs), comprising a 1× dilution of each of:
   (a) a 100× solution comprising: 10.5 g/L±10% L-arginine hydrochloride, 7.88 g/L±10% L-Asparagine $H_2O$, 1.147 g/L±10% Choline chloride, 2.622 g/L±10% L-Histidine HCl, 3.38 g/L±10% L-isoleucine (allo-free), 4.92 g/L±10% L-Leucine, 6.39 g/L±10% L-Lysine HCL, 1.086 g/L±10% L-Methionine, 2 g/L±10% L-Phenylalanine, 1.15 g/L±10% L-Proline, 2.89 g/L±10% L-Serine, 4.46 g/L±10% L-Threonine, 0.757 g/L±10% L-Tryptophan, 0.453 g/L±10% L-Tyrosine, 2.79 g/L±10% L-Tyrosine Disodium Salt Dihydrate, 4.4 g/L±10% L-Valine, and;
   (b) a 100× solution comprising 0.5 mg/L±10% d-Biotin, 0.133 g/L±10% folinic acid (Ca2+ salt), 0.3 mg/L±10% folic acid, 0.407 g/L±10% Niacinamide, 0.124 g/L±10% Pantothenic Acid (Hemi-calcium salt), 0.103 g/L±10% Pyridoxine HCl, 0.126 g/L±10% Thiamine HCl, 0.041 g/L±10% Vitamin B12;
   (c) a 100× solution comprising 32.86 g/L±10% L-Glutamine;
   (d) a 100× solution comprising 8.25 g/L±10% sodium pyruvate;
   (e) a 100× solution comprising 1.5 g/L±10% L-Cysteine HCl $H_2O$
   (f) a 100× solution comprising 0.668 g/L±10% L-Alanine, 0.998 g/L±10% L-Aspartic acid, 1.103 g/L±10% L-Glutamic acid, 1.312 g/L±10% Glycine;
   (g) a 100× solution comprising 0.00675 g/L±10% adenine, 1.5 g/L±10% myo-inositol, 0.00535 g/L±10% Lipoic Acid, 0.022 g/L±10% thymidine, 0.004 g/L±10% putrescine 2HCl;
   (h) a 200× solution of 41.06 g/L±10% $CaCl_2$) $2H_2O$;
   (i) a 200× solution of 44.54 g/L±10% $MgSO_4$ $7H_2O$;
   (j) a 200× solution of 0.1807 g/L±10%, $FeSO_4$ $7H_2O$;
   (k) a 100× solution comprising 0.077 mg/L±10% $CuSO_4$ $5H_2O$, 0.19 mg/L±10% $H_2SeO_3$, 0.006 mg/L±10% $MnSO_4$ $5H_2O$, 0.71 g/L±10% $NaSiO_3$ 9 $H_2O$, 0.062 mg/L±10% (NH$_4$)MO$_7$O$_{24}$ 4H$_2$O, 0.0293 mg/L±10% NH$_4$VO$_3$, 0.00006 mg/L±10% NiCl$_2$ 6H$_2$O, 0.0000564 mg/L±10% SnCl$_2$ 2H$_2$O, and 0.029 g/L±10% ZnSO$_4$7H$_2$O; and (l) a 100× solution of 0.0166 g/L±10% riboflavin, wherein the basal medium supports growth of human mammary epithelial cells (HMECs) as pre-stasis finite cells for up to 60 population doublings.

2. The basal medium of claim 1, further comprising HEPES buffer, NaOH, and D-glucose.

3. An optimized cell culture medium, comprising:
the basal medium of claim 1; and
serum, a growth factor, or both.

4. The optimized medium of claim 3, comprising serum and a growth factor.

5. A method of making the basal medium according to claim 1, the method comprising combining stock solutions (a)-(l) with water in a container to produce the basal medium comprising a 1× dilution of the stock solutions (a)-(l).

6. The method according to claim 5, further comprising, after the combining, sterilizing the basal medium.

7. The basal medium of claim 1, wherein the medium is free of conditioned medium.

8. A method for culturing epithelial cells, comprising the step of culturing the normal human epithelial cells with a culture medium comprising the basal medium according to claim 1, for a period of time over which at least 10 population doublings of the normal HMECs occurs during the culturing.

9. The basal medium of claim 1, further comprising normal human mammary epithelial cells (HMECs).

* * * * *